United States Patent [19]  [11] 4,371,547
Münzenmaier et al.  [45] Feb. 1, 1983

[54] 2-BENZYLIDENEGLUTARALDEHYDES USEFUL AS DISINFECTANTS

[75] Inventors: Wolfgang Münzenmaier, Wennigsen; Heinz Eggensperger, Hamburg; Helmut H. Ehlers, Hamburg; Wolfgang Beilfuss, Hamburg; Lothar Bücklers, Norderstedt; Hans-Peter Harke, Hamburg, all of Fed. Rep. of Germany

[73] Assignee: Sterling Drug Inc., New York, N.Y.

[21] Appl. No.: 294,890

[22] Filed: Aug. 21, 1981

[30] Foreign Application Priority Data

Aug. 30, 1980 [DE] Fed. Rep. of Germany ...... 3032794

[51] Int. Cl.³ ............... C07C 47/548; A61K 31/11; C07C 143/38; C07C 143/44
[52] U.S. Cl. .................................. 424/333; 562/463; 562/459; 424/324; 562/458; 562/457; 424/317; 562/456; 562/455; 424/315; 562/453; 562/452; 424/309; 562/438; 562/437; 424/308; 562/435; 562/434; 424/304; 564/169; 564/166; 260/511; 564/156; 564/155; 260/510; 564/153; 549/417; 260/509; 542/449; 260/508; 260/507 R; 260/465 R; 260/465 D; 260/465 F; 260/465 G; 260/465 H; 260/465 K; 568/442; 568/425; 568/424; 560/12; 560/14; 560/20; 560/21; 560/22; 560/23; 560/46; 560/47; 560/48; 560/51; 560/53; 560/54
[58] Field of Search ............. 260/511, 510, 509, 508, 260/507 R, 465 R, 465 D, 465 F, 465 G, 465 H, 465 K; 568/425, 442, 424; 560/12, 14, 20, 21, 22, 23, 46, 47, 48, 51, 53, 54; 562/463, 459, 458, 457, 456, 455, 453, 452, 438, 437, 435, 434; 564/153, 155, 156, 166, 169; 424/333, 324, 317, 315, 309, 308, 304

[56] References Cited
U.S. PATENT DOCUMENTS
4,122,192 10/1978 Fellons .............................. 424/333

OTHER PUBLICATIONS

F. Weiss et al., "Recherches sur les acetals. II.-Rearrangements thermiques de methylene-5 dioxannes-1,3 en esters methallyliques et en α-methyleneglutaraldehydes," Bull. Soc. Chim. France, 1965, 1358.
R. L. Garnick et al., "Biomimetic Transformations among Monomeric Macroline-Related Indole Alkaloids," J. Amer. Chem. Soc., 100, 4215, 4218, (1978).
K. C. Brannock, "Preparation of 2,6-Dialkoxy-3-(-1-alkoxyalkyl)-tetrahydropyrans," J. Org. Chem. 24, 1382–1383, (1959).
R. K. Murray, Jr. et al., "On the Photochemistry of 1-Oxaspiro[2.n]alkan-5-ones," J. Org. Chem. 42, 3994–3997, (1977).
H. A. Burch, "Dioxanes, Dithianes, and Oxathianes," Chem. Abstracts 63, P18108a, (1965).
A. Losse et al., "Condensation of Acetaldehyde and Crotonaldehyde," Chem. Abstracts 68, 48984e, (1968).
F. Camps et al., "Formation of carbocycles in the condensation of crotonaldehyde. II. Synthesis of (E)-2-ethylidene-3-methylpentane-dial (dicrotonaldehyde)," Chem. Abstracts 79, 41831w, (1973).

Primary Examiner—Nicky Chan
Attorney, Agent, or Firm—Frederik W. Stonner; B. Woodrow Wyatt

[57] ABSTRACT

2-Benzylideneglutaraldehydes of the formula $$OCH-CH_2-CH_2-\underset{\underset{CH}{\|}}{C}-CHO$$

[benzene ring with substituents $R^1$, $R^2$, $R^3$]

wherein $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy, a method of use thereof as disinfectants, disinfectant compositions comprising them, and 2,6-dialkoxy-3-(α-alkoxybenzyl)tetrahydropyrans of the formula

[structure with benzene ring bearing $R^1$, $R^2$, $R^3$ and tetrahydropyran with $R^4O$, $OR^5$, $CH-OR^5$]

where $R^1$, $R^2$ and $R^3$ are as defined above and $R^4$ and $R^5$ independently are alkyl of one to four carbon atoms, which are intermediates for their preparation are disclosed.

23 Claims, No Drawings

2-BENZYLIDENEGLUTARALDEHYDES USEFUL AS DISINFECTANTS

BACKGROUND OF THE INVENTION

1. Field of the Invention

The invention relates to novel glutaraldehydes to their use as disinfectants, and to novel intermediates for their preparation.

2. Description of the Prior Art

It is known that aldehydes such as formaldehyde, glyoxal and glutaraldehyde have disinfecting action and therefore are used in disinfectants. However, there are various disadvantages in the use of these aldehydes. For example, although glyoxal is odorless and a good surface disinfectant, it is not sufficiently active in suspension tests. Other aldehydes, such as formaldehyde or glutaraldehyde, although quite active, are limited in their application and in-use concentration because of their penetrating and obnoxious odor. Furthermore, because of their volatility, their toxicologic effects must be considered.

The formation of resistant microbial strains and the process of natural selection require the preparation of ever new agents which supplement the activity of known disinfectant products or enhance their activity against such resistant strains. The preparation of new agents makes it possible to substitute them for presently used disinfectants and thereby decrease the formation of resistant strains.

There is a need therefore for agents which are highly active as disinfectants, are essentially odorless or have a pleasant odor, and have low volatility.

Certain 2-alkylideneglutaraldehydes are described in the art. See for example, Bull. Soc. Chim. France, 1965, 1358, J. Amer. Chem. Soc. 100, 4215, 4218 (1978), J. Org. Chem. 24, 1382-3 (1959) and 42, 3994-7 (1977), and Chem. Abstracts 63, P18108a (1965), 68, 48984e (1968) and 79, 41831w (1973). No biological utility for the 2-alkylideneglutaraldehydes is disclosed in the foregoing references.

Certain 2,6-dialkoxy-3-(1-alkoxyalkyl)tetrahydropyrans are disclosed in J. Org. Chem. 24, 1382-3 (1959). This reference discloses that the 2,6-dialkoxy-3-(1-alkoxyalkyl)tetrahydropyrans are readily converted by known methods to 2-alkylideneglutaraldehydes.

SUMMARY OF THE INVENTION

It has now been discovered that benzylideneglutaraldehyde, which may be substituted in the benzene ring, has antibacterial properties superior to glutaraldehyde. Microbiological investigations indicate excellent activity in suspension tests (Table 1), including tests with a 20% serum load (Table 2). Especially to be noted is the extraordinary activity against fungi, which is clearly greater than that of glutaraldehyde (Table 3).

Thus, in one aspect of the invention there is provided a 2-benzylideneglutaraldehyde represented by the formula

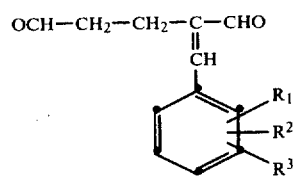

where $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy.

In another aspect of the invention there is provided a composition for disinfecting an inanimate surface comprising as an active ingredient an amount effective for disinfecting said inanimate surface of a 2-benzylideneglutaraldehyde represented by the formula

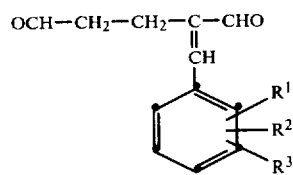

where $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy, and a carrier for said active ingredient.

In yet another aspect of the invention there is provided a method for disinfecting an inanimate surface contaminated with deleterious microorganisms which comprises contacting said surface with an amount effective for disinfection thereof of a 2-benzylideneglutaraldehyde represented by the formula

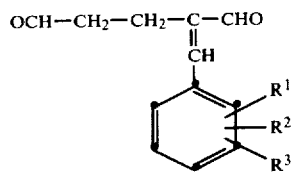

where $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy.

In a further aspect of the invention there is provided a 2,6-dialkoxy-3-(α-alkoxybenzyl)tetrahydropyran represented by the formula

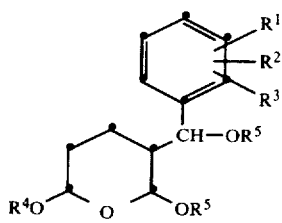

where $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy; and $R^4$ and $R^5$ independently are alkyl of one to four carbon atoms.

The compounds of Formula I exhibit antibacterial and antifungal activities and are useful as antifungal and antibacterial agents, e.g., in disinfectant compositions.

The compounds of Formula II are useful as intermediates in the preparation of the compounds of Formula I.

DETAILED DESCRIPTION INCLUSIVE OF THE PREFERRED EMBODIMENTS

Compared to presently used aldehydes, the novel 2-benzylideneglutaraldehydes of the invention are almost odorless even in pure form, an essential feature as already noted before. With the novel 2-benzylideneglutaraldehydes, disinfectant compositions can be prepared containing higher concentrations of active ingredient than heretofor possible with the known aldehydes. Such disinfectant compositions possess a pleasant odor as concentrates and are almost odorless in use-solution so that they are useful over a wide range of concentrations.

Halo as used herein refers to bromo, chloro, iodo and fluoro.

Lower-alkyl and lower-alkoxy as used herein refer to such groups having from one to six carbon atoms which may be arranged in straight or branched chains such as methyl, ethyl, propyl, isopropyl, butyl, isobutyl, pentyl and hexyl for lower-alkyl and methoxy, ethoxy, propoxy, isopropoxy, butoxy, tertiary-butoxy, pentoxy and hexyloxy for lower-alkoxy.

In the compounds of formula II, alkyl, as represented by $R^4$ and $R^5$, can be arranged in a straight or branched chain such as methyl, ethyl, propyl, isopropyl, butyl and isobutyl.

The substituents represented by $R^1$, $R^2$ and $R^3$ can occur at any of the available positions of the benzene ring of the compounds of formulas I and II and where there is more than one such substituent, they can be the same or different and can occur in any position combination relative to each other.

The free acid forms of the compounds of formulas I and II where any of $R^1$, $R^2$ and $R^3$ represent carboxy and/or hydroxysulfonyl are convertible to the corresponding salt form by interaction with a particular base and such salts are considered to be the full equivalents of the acids. Examples of such salts are the alkali metal salts such as the sodium and potassium salts.

The 2-benzylideneglutaraldehydes of the invention can be prepared by a well known procedure. Thus, they can be prepared by condensation of a benzaldehyde acetal represented by the formula

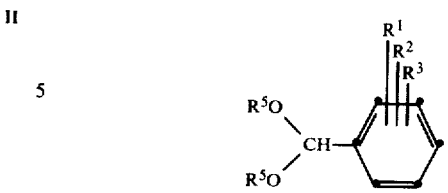

where $R^1$, $R^2$, $R^3$ and $R^5$ are as defined hereinabove, with a 2-alkoxy-2,3-dihydro-4H-pyran represented by the formula

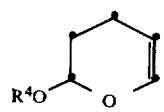

where $R^4$ is as defined hereinabove, in the presence of a Lewis acid such as zinc chloride or boron trifluoride to give the corresponding novel 2,6-dialkoxy-3-(α-alkoxybenzyl)tetrahydropyran of formula II followed by hydrolysis of the latter. The condensation reaction results in surprisingly high yield, so that in many cases a purification step is not necessary. Because essentially no by-products are formed, the crude condensation product can be used without distillation in the subsequent hydrolysis step, which is essential for economical preparation of the 2-benzylideneglutaraldehydes.

The hydrolysis of the 2,6-dialkoxy-3-(α-alkoxybenzyl)tetrahydropyrans can be carried out with acids in aqueous dioxane, although aqueous solutions which contain acidic emulsifying agents also are suitable, as are acidic solutions containing emulsifying agents. These solutions may be used directly for the formulation of disinfectant compositions after adjustment to the desired pH. Such solutions additionally contain the partially hydrolyzed products 2-(α-alkoxybenzyl)-glutaraldehyde and 3-benzylidene-2,6-dialkoxytetrahydropyran represented respectively by the formulas

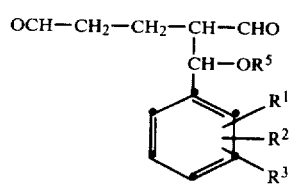

and

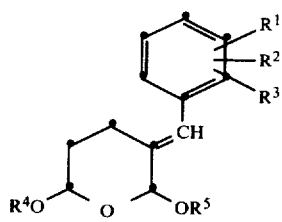

where $R^1$, $R^2$, $R^3$, $R^4$ and $R^5$ are as defined hereinabove.

The antibacterial actions of disinfectant compositions which contain the 2-benzylideneglutaraldehyde on one hand and on the other hand additionally contain the partial hydrolysis products III and IV, in corresponding concentrations, are equivalent within the range of normal limits of error (Tables 5 and 6 hereinbelow). Therefore, distillation of the 2-benzylideneglutaraldehydes, which results in decreased yields and increased cost, is not necessary for the preparation of the disinfectant compositions of the invention.

The pure 2-benzylideneglutaraldehydes are colorless to yellowish liquids, which become partly crystalline after some time. They are insoluble in water, but can be dissolved in the usual organic solvents. These include, for example, the lower alcohols, such as ethanol, propan-2-ol, propan-1-ol, and also glycols, such as ethylene glycol and triethyleneglycol as well as glycol derivatives such as propylene glycol. On prolonged standing the pure 2-benzylideneglutaraldehydes may polymerize, but on addition of acid the monomeric aldehydes are regenerated.

The 2,6-dialkoxy-3-($\alpha$-alkoxybenzyl)tetrahydropyrans also are mostly viscous, colorless to yellowish oils which are soluble in the usual organic solvents but not in water.

The benzaldehyde acetal starting materials are known compounds or can be readily prepared by well known procedures, e.g., by condensation of the appropriate benzaldehyde with an appropriate trialkylorthoformate.

The 2-alkoxy-2,3-dihydro-4H-pyran starting materials are known compounds or can be readily prepared by well known procedures, e.g., by condensation of an appropriate alkyl vinyl ether with acrolein.

In preparing the disinfectant compositions of the invention, the 2-benzylideneglutaraldehydes can be formulated in either acid or basic medium. The pH of the compositions should range from about 4 to 8, preferably 5 to 7. This can be achieved by the addition of acidic agents, e.g., mineral acids such as hydrochloric and sulfuric acids, or organic acids such as citric or tartaric acids, or acidic emulsifying agents such as alkylsulfonic acid, or alkaline agents such as sodium hydroxide, alkali carbonate or organic amines, such as triethanolamine.

The disinfectant compositions of the invention can be formulated as aqueous or non-aqueous solutions employing suitable solvents as carries. Such solvents are for example primary, secondary or tertiary mono or multifunctional aliphatic alcohols such as methanol, ethanol, propan-2-ol, propan-1-ol, ethylene glycol and glycerol.

The disinfectant compositions additionally can contain optional ingredients such as mono- or dialdehydes, e.g., formaldehyde, glyoxal or glutaraldehyde; surfactants of the class of anionic, non-ionic, cationic and amphoteric detergents; and antibacterially active organic acids, such as lactic acid, citric acid, which can also be used to adjust the pH; and particular antimicrobial trisubstituted phenols, e.g., 2,6-dimethyl-4-bromophenol.

The disinfectant compositions of the invention have outstanding stability. On prolonged storage, no change in the physical characteristics of the compositions or loss in efficacy are discernable.

The 2-benzylideneglutaraldehydes of the invention and the disinfectant compositions containing them can be employed for the disinfection of a wide variety of inanimate surfaces contaminated with deleterious microorganisms such as are found in industrial, domestic and medical environments. For example, in a hospital environment they can be used to disinfect walls, floors and work surfaces as well as utensils such as bedpans, etc. They are particularly useful in the medical field, i.e., in human and veterinary medicine and surgery and in dentistry for disinfection of a wide variety of objects made from or containing rubber, plastic, metal and ceramics, e.g., instruments, devices and equipment such as lensed instruments, fiberoptic devices, anesthesia equipment, inhalation equipment, catheters, scalpels, scissors, forceps, needles, syringes, clamps, thermometers, etc. Such surfaces can be disinfected by contacting them with an antimicrobially effective amount of the 2-benzylideneglutaraldehyde using appropriate techniques well known in the art such as, for example, immersion, spraying, swabbing, etc. The amount of 2-benzylideneglutaraldehyde to be employed in a particular disinfectant composition of the invention and the contact time with the surface required to effect disinfection will depend on various factors such as the type of surface and the degree of contamination of the surface, and can readily be determined by one having ordinary skill in the art.

The invention is illustrated by the following examples without, however, being limited thereto.

EXAMPLE 1

(a) 2,6-Dimethoxy-3-($\alpha$-methoxybenzyl)tetrahydropyran 152 g. (1.0 mole) benzaldehyde dimethyl acetal was combined with 3 g. $ZnCl_2$. While stirring and cooling to 25° C., 114 g. (1 mole) 2-methoxy-2,3-dihydro-4H-pyran was added. After stirring for an hour, the catalyst was neutralized by the addition of 15 g. potassium carbonate in 30 ml. water. The mixture was then extracted with ether and the combined ether extracts were washed with water and dried over sodium sulfate. After the removal of the solvent, the residue was distilled in vacuo to give the title compound; b.p. 120°–128° C. (0.6 mm). Yield: 243 g. (91%).

Following a procedure analogous to that of Example 1(a) and using 2-chlorobenzaldehyde diethyl acetal and 2-ethoxy-2,3-dihydro-4H-pyran, there was obtained 2,6-diethoxy-3-($\alpha$-ethoxy-2-chlorobenzyl)tetrahydropyran in 90% yield; b.p. 140° C. (0.01 mm).

Following a procedure analogous to that of Example 1(a) and using 4-methoxybenzaldehyde diethyl acetal and 2-ethoxy-2,3-dihydro-4H-pyran there was obtained 2,6-diethoxy-3-($\alpha$-ethoxy-4-methoxybenzyl)tetrahydropyran in 81% yield; b.p. 156°–159° C. (0.01 mm).

(b) 2-Benzylideneglutaraldehyde

A mixture of 100 g. 2,6-dimethoxy-3-($\alpha$-methoxybenzyl)tetrahydropyran, 300 g. dioxane, 200 ml. water and 40 g. concentrated hydrochloric acid was stirred for 2 hours at 60°–70° C. The solution, which eventually became homogeneous and brown colored, was cooled, neutralized with sodium bicarbonate and the organic layer was separated. The aqueous layer was extracted twice with ether and the combined organic phase was washed until neutral. The solvent was removed and the residue was distilled in vacuo to give 51 g. of the title compound; b.p. 132° C. (1 mm). Yield: 51 g. (73%) (distillation was accompanied by partial decomposition).

Following a procedure analagous to that of Example 1(b) but using respectively 2,6-diethoxy-3-($\alpha$-ethoxy-2-chlorobenzyl)tetrahydropyran and 2,6-diethoxy-3-($\alpha$-ethoxy-4-methoxybenzyl)tetrahydropyran there was obtained respectively 2-(2-chlorobenzylidene)-glutaraldehyde, b.p. 155° C. (0.8 mm), yield: 57%; and 2-(4-methoxybenzylidene)glutaraldehyde, b.p. 175° C. (1.0 mm), yield 61%.

EXAMPLE 2

Preparation of a 10% solution of 2-benzylideneglutaraldehyde without isolation of intermediates 2,6-Dimethoxy-3-(α-methoxybenzyl)tetrahydropyran was prepared according to the procedure of Example 1(a) and used in the next step without distillation. 30 g. Dodecylbenzenesulfonic acid (Marlon AS 3; Chemische Werke Hülls A.G., Marl, W. Germany) was added to 100 g. crude product followed by 50 g. triethyleneglycol and 250 g. water. The mixture was heated for 30 minutes to 95° C., neutralized and an additional 136 g. sodium dodecylbenzenesulfonate (Phenylsulfonat HSR KONZ; Hoechst A. G., Frankfurt, W. Germany) was added. On addition of 150 g. water, an approximately 10% solution of 2-benzylideneglutaraldehyde and corresponding hydrolysis precursors of formulas III and IV was obtained.

The microbiological investigation of the individual compounds was carried out in aqueous solution which in addition to 10% of the 2-benzylideneglutaraldehyde to be tested, contained 5% isopropyl alcohol, 5% triethyleneglycol and 18% of a sodium alkanesulfonate ($C_{10}$–$C_{18}$) (Mersolat W93; Bayer A. G., Leverkusen, W. Germany).

The microbiological tests were carried out according to the specifications for the testing of chemical disinfectants of the German Society for Hygiene and Microbiology (3rd Edition, 1972). The test results are recorded in Tables 1 to 6 below.

TABLE 1

Bactericidal Activity (suspension test) (killing time in minutes)

| | Concentration (Vol. %) (active ingredient) | Staphylococcus aureus | Klebsiella pneumoniae | Pseudomonas aeruginosa | Proteus vulgaris |
|---|---|---|---|---|---|
| 2-Benzylidene-glutaraldehyde | 0.1 | 2.5 | 2.5 | 2.5 | 2.5 |
| | 0.05 | 2.5 | 2.5 | 2.5 | 2.5 |
| | 0.025 | 2.5 | 2.5 | >30 | 2.5 |
| | 0.01 | 15 | 30 | | 30 |
| 2-(2-Chloro-benzylidene) glutaraldehyde | 0.25 | 2.5 | 2.5 | 2.5 | 2.5 |
| | 0.1 | 2.5 | 2.5 | 15 | 5 |
| | 0.05 | 2.5 | 2.5 | >30 | 5 |
| | 0.025 | 2.5 | 15 | | 5 |
| | 0.01 | 2.5 | >30 | | >30 |
| | 0.005 | 2.5 | | | |
| | 0.0025 | 5 | | | |
| Glutaraldehyde | 0.2 | 2.5 | 5 | 5 | 15 |
| | 0.1 | 5 | 15 | 15 | 30 |
| | 0.05 | 15 | 15 | 30 | 30 |
| | 0.025 | >30 | >30 | >30 | >30 |
| Glyoxal | 0.5 | >30 | | >30 | >30 |

TABLE 2

Bactericidal Activity With A 20% Serum Load (suspension test) (killing time in minutes)

| | Concentration (Vol. %) (active ingredient) | Staphylococcus aureus | Klebsiella pneumoniae | Pseudomonas aeruginosa | Proteus vulgaris |
|---|---|---|---|---|---|
| 2-Benzylidene-glutaraldehyde | 0.25 | 2.5 | 2.5 | 2.5 | 2.5 |
| | 0.1 | 2.5 | 2.5 | >30 | 2.5 |
| | 0.05 | 15 | 30 | | 2.5 |
| | 0.025 | 15 | >30 | | 30 |
| Glutaraldehyde | 0.2 | 2.5 | 2.5 | 5 | 2.5 |
| | 0.1 | 5 | 5 | >30 | 30 |
| | 0.05 | >30 | 30 | | 30 |

TABLE 3

Fungicidal Activity (suspension test) (killing time in minutes)

| | Concentration (Vol. %) (active ingredient) | Trichophyton mentagrophytes | Candida albicans | Aspergillus niger |
|---|---|---|---|---|
| 2-Benzylidene-glutaraldehyde | 0.05 | 2.5 | 2.5 | 2.5 |
| | 0.025 | 2.5 | 2.5 | 5 |
| | 0.01 | 2.5 | 2.5 | 15 |
| | 0.005 | 2.5 | 15 | >30 |
| | 0.0025 | 15 | >30 | |
| | 0.001 | >30 | | |
| 2-(2-Chloro-benzylidene)-glutaraldehyde | 0.05 | 2.5 | 2.5 | 30 |
| | 0.025 | 2.5 | 2.5 | >30 |
| | 0.01 | 2.5 | 2.5 | |
| | 0.005 | 2.5 | >30 | |
| | 0.0025 | 5 | | |
| | 0.001 | 15 | | |
| Glutaraldehyde | 0.2 | 2.5 | 30 | 30 |
| | 0.1 | 2.5 | 30 | |
| | 0.05 | 5 | 30 | |
| | 0.03 | 15 | | |
| | 0.01 | 30 | | |

TABLE 4

Surface Activity (killing time in hours)

| | Concentration (Vol. %) (active ingredient) | Staphylococcus aureus | | Escherichia coli | |
|---|---|---|---|---|---|
| | | PVC | Wood Lacquer | PVC | Wood Lacquer |
| 2-Benzylidene-glutaraldehyde | 0.5 | 1 | 1 | 1 | 1 |
| | 0.2 | 1 | 1 | 1 | 1 |
| | 0.1 | 6 | 6 | 1 | 1 |
| | 0.05 | >6 | >6 | >6 | >6 |
| Glutaraldehyde | 0.2 | 1 | 1 | 1 | 1 |
| | 0.1 | >6 | >6 | 4 | 4 |
| | 0.05 | | | 6 | 6 |

TABLE 4-continued

| Surface Activity (killing time in hours) | | | | |
|---|---|---|---|---|
| Concentration (Vol. %) (active ingredient) | *Staphylococcus aureus* | | *Escherichia coli* | |
| | PVC | Wood Lacquer | PVC | Wood Lacquer |
| Glyoxal 0.1 | 1 | 1 | 1 | 1 |
| 0.05 | 2 | 2 | 2 | 1 |
| 0.01 | >6 | >6 | >6 | >6 |

TABLE 5

Bactericidal activity of a solution of 2-benzylideneglutaraldehyde prepared according to Example 2 (suspension test) killing time in minutes)

| Concentration (Vol. %) (active ingredient) | *Staphylococcus aureus* | *Klebsiella pneumoniae* | *Pseudomonas aeruginosa* | *Proteus vulgaris* |
|---|---|---|---|---|
| 0.25 | 2.5 | 2.5 | 2.5 | 2.5 |
| 0.1 | 2.5 | 2.5 | 15 | 2.5 |
| 0.05 | 2.5 | 2.5 | >30 | 2.5 |
| 0.025 | 5 | 15 | | 2.5 |
| 0.01 | 15 | >30 | | 15 |

TABLE 6

Fungicidal activity of a solution of 2-benzylideneglutaraldehyde prepared according to Example 2 (suspension test) (killing time in minutes)

| Concentration (Vol. %) (active ingredient) | *Trichophyton mentagrophytes* | *Candida albicans* | *Aspergillus niger* |
|---|---|---|---|
| 0.1 | 2.5 | 2.5 | 5 |
| 0.05 | 2.5 | 2.5 | 15 |
| 0.025 | 2.5 | 2.5 | 30 |
| 0.01 | 2.5 | 2.5 | >30 |
| 0.005 | 2.5 | 2.5 | |
| 0.001 | 5 | >30 | |

We claim:

1. A 2-benzylideneglutaraldehyde represented by the formula

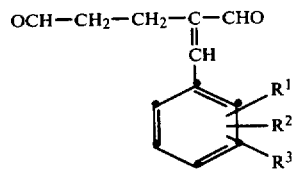

where $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy.

2. A 2-benzylideneglutaraldehyde according to claim 1 where $R^1$, $R^2$ and $R^3$ independently are hydrogen or a substituent selected from the group consisting of halo, lower-alkyl and lower-alkoxy.

3. A 2-benzylideneglutaraldehyde according to claim 2 where $R^2$ and $R^3$ each is hydrogen.

4. A 2-benzylideneglutaraldehyde according to claim 2 where $R^1$, $R^2$ and $R^3$ independently are hydrogen or a substituent selected from the group consisting of halo and lower-alkoxy.

5. A 2-benzylideneglutaraldehyde according to claim 4 where $R^2$ and $R^3$ each is hydrogen.

6. A 2-benzylideneglutaraldehyde according to claim 5 where $R^1$ is hydrogen or the substituent chloro or methoxy.

7. 2-Benzylideneglutaraldehyde according to claim 6.

8. 2-(2-Chlorobenzylidene)glutaraldehyde according to claim 6.

9. 2-(4-Methoxybenzylidene)glutaraldehyde according to claim 6.

10. A composition for disinfecting an inanimate surface comprising as an active ingredient an amount effective for disinfecting said inanimate surface of a 2-benzylideneglutaraldehyde represented by the formula

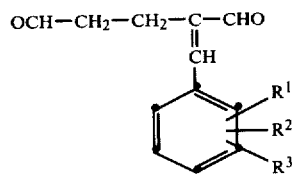

where $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy, and a carrier for said active ingredient.

11. A composition according to claim 10 wherein $R^1$, $R^2$ and $R^3$ independently are hydrogen or a substituent selected from the group consisting of halo, lower-alkyl and lower-alkoxy.

12. A composition according to claim 11 where $R^2$ and $R^3$ each is hydrogen.

13. A composition according to claim 11 where $R^1$, $R^2$ and $R^3$ independently are hydrogen or a substituent selected from the group consisting of halo and lower-alkoxy.

14. A composition according to claim 13 where $R^2$ and $R^3$ each is hydrogen.

15. A composition according to claim 14 where $R^1$ is hydrogen or the substituent chloro or methoxy.

16. A composition according to claim 15 where said active ingredient is selected from the group consisting of 2-benzylideneglutaraldehyde, 2-(2-chlorobenzylidene)glutaraldehyde and 2-(4-methoxybenzylidene)glutaraldehyde.

17. A method for disinfecting an inanimate surface contaminated with deleterious microorganisms which comprises contacting said surface with an amount effective for disinfection thereof of a 2-benzylideneglutaraldehyde represented by the formula

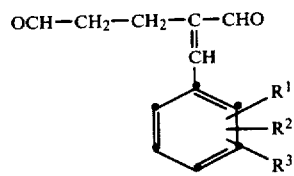

where $R^1$, $R^2$ and $R^3$ independently are hydrogen or a substituent selected from the group consisting of halo, lower-alkyl, phenyl, carboxy, lower-alkoxycarbonyl, phenoxycarbonyl, aminocarbonyl, hydroxysulfonyl, nitro, cyano, hydroxy, lower-alkoxy and phenoxy.

18. A method according to claim 17 where $R^1$, $R^2$ and $R^3$ independently are hydrogen or a substituent selected from the group consisting of halo, lower-alkyl and lower-alkoxy.

19. A method according to claim 18 where $R^2$ and $R^3$ each is hydrogen.

20. A method according to claim 18 where $R^1$, $R^2$ and $R^3$ independently are hydrogen or a substituent selected from the group consisting of halo and lower-alkoxy.

21. A method according to claim 20 where $R^2$ and $R^3$ each is hydrogen.

22. A method according to claim 21 where $R^1$ is hydrogen or the substituent chloro or methoxy.

23. A method according to claim 22 where the 2-benzylideneglutaraldehyde is selected from the group consisting of 2-benzylideneglutaraldehyde, 2-(2-chlorobenzylidene)glutaraldehyde and 2-(4-methoxybenzylidene)glutaraldehyde.

* * * * *